United States Patent [19]
Cook

[11] Patent Number: 4,789,783
[45] Date of Patent: Dec. 6, 1988

[54] DISCHARGE IONIZATION DETECTOR

[76] Inventor: Robert D. Cook, 1137 Hill Slope Pl., Los Altos, Calif. 94022

[21] Appl. No.: 33,256

[22] Filed: Apr. 2, 1987

[51] Int. Cl.⁴ .............................................. H01J 7/24
[52] U.S. Cl. ................... 250/379; 250/385.1
[58] Field of Search ................... 250/374, 379, 385 R; 324/464

[56] References Cited

U.S. PATENT DOCUMENTS

| | | |
|---|---|---|
| 3,087,113 | 4/1963 | Foster . |
| 3,264,511 | 8/1966 | Yamasaki . |
| 3,348,447 | 10/1967 | Goleb . |
| 3,378,725 | 4/1968 | Bochinski et al. . |
| 3,418,514 | 12/1968 | Sternberg . |
| 3,425,806 | 2/1969 | Karmen . |
| 3,602,716 | 8/1971 | Matousek et al. . |
| 3,685,911 | 8/1972 | Dahlquist et al. . |
| 4,013,913 | 3/1977 | Driscoll et al. . |
| 4,028,617 | 6/1977 | Kamo et al. .................. 324/464 |
| 4,266,196 | 5/1981 | Kawazoe et al. . |
| 4,366,418 | 12/1982 | Mayama et al. . |

OTHER PUBLICATIONS

Villalobos, Use and Applications of a Nonradioactive Helium Ionization Detector in Process Gas Chromatography, *ISA Transactions*, vol. 7, No. 1, (1968).

*Primary Examiner*—Gene Wan
*Attorney, Agent, or Firm*—Arnold, White & Durkee

[57] ABSTRACT

A discharge ionization detector has a detector body with first and second chambers and an interconnecting aperture passageway. A glow discharge emission in the first chamber is directed through the aperture to cause ionization of column effluent species in the second chamber. A polarizing electrode creates an electric field to cause acceleration of ionized species toward a collector electrode coupled to an electrometer. The detector body is of an electrically-conductive material and is coupled to ground potential to reduce entry of glow discharge-produced electrons into the second chamber.

4 Claims, 4 Drawing Sheets

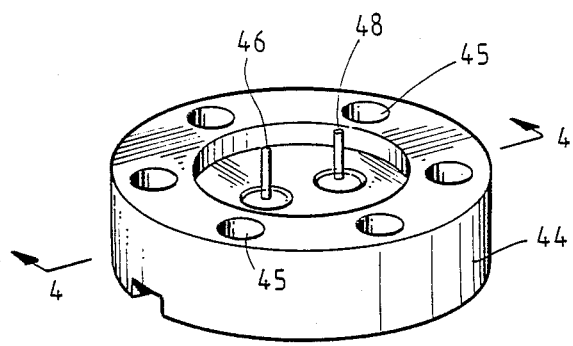
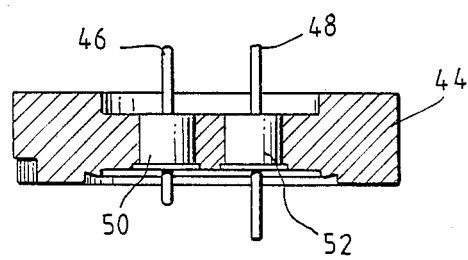
Fig. 3
Fig. 4
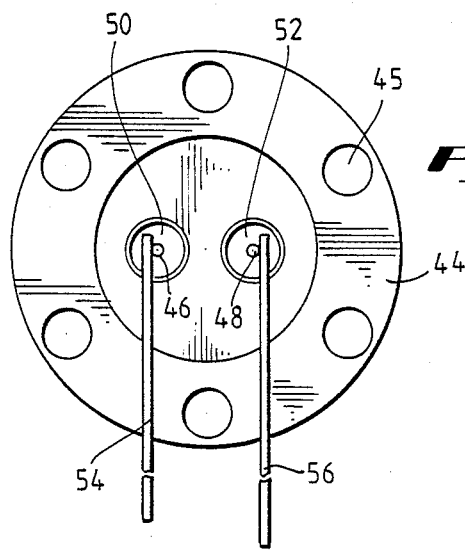
Fig. 5A
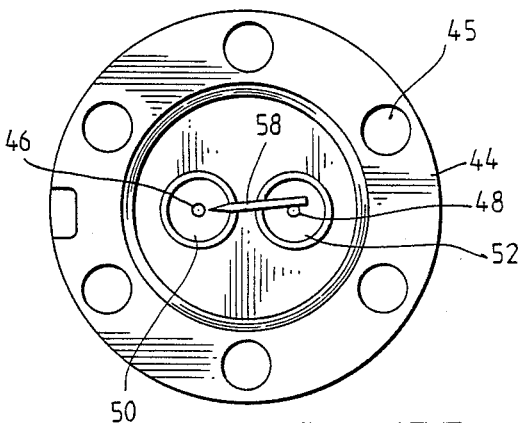
Fig. 5C
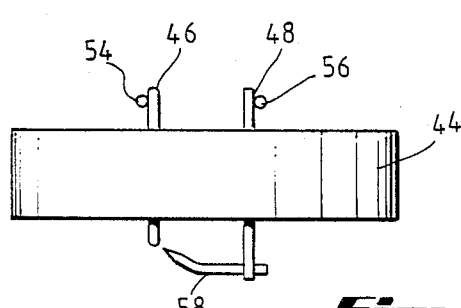
Fig. 5B

DISCHARGE IONIZATION DETECTOR

BACKGROUND OF THE INVENTION

The present invention relates to detectors for gas chromatography; and more particularly, it relates to discharge ionization detectors which provide an output indication functionally related to the quantity of ionizable material present in the column effluent from a gas chromatograph.

Helium ionization detectors using a nonradioactive source of ionizing radiation have been found to be stable and reliable. Further, such detectors have very good sensitivity. The principle of operation of the detector is based upon the use of photons to produce ionic species. A high voltage imposed across discharge electrodes in a chamber produces a glow discharge. In the presence of helium, a characteristic discharge emission of photons occurs. The photons irradiate a port connecting the discharge chamber to an ionization chamber receiving the gas chromatograph column effluent. Electrons are produced in the ionization chamber as a result of photon interaction with ionizable molecules in the column effluent. Electrons produced by the glow discharge are repelled by a negatively charged polarizing electrode. Electrons produced in the ionization chamber are attracted to a collector electrode and result in a current to an electrometer.

SUMMARY OF THE INVENTION

A discharge ionization detector in accordance with the present invention comprises a detector body defining first and second chamber wells coaxially disposed and having a common internal wall with an aperture therein. The body includes an inlet to the first chamber well for admitting an emission gas, and an inlet to the second chamber well for admitting the column effluent of a chromatograph. A first electrode assembly including a flange to be mounted to the detector body closes the first chamber well, and has a pair of electrodes for generating a glow discharge emission directed through the aperture into the second chamber well to cause ionization of species in the column effluent. A second electrode assembly including a flange to be mounted to the detector body closes the second chamber well, and has a collector electrode, to be coupled to an electrometer providing an indication of ionized species in the column effluent, and a polarizing electrode, to be negatively charged, for generating an electric field with respect to the collector electrode to cause electrons to be accelerated toward the collector electrode. The column effluent inlet to the second chamber well directs the flow of column effluent transversely to the discharge emission directed through the aperture. The polarizing electrode disposed within the second chamber is substantially aligned with the column effluent inlet and is of an annular configuration oriented in a plane transverse to the discharge emission. The collector electrode is disposed in substantially coaxial alignment with the aperture. The detector body is coupled to ground potential, to reduce entry of glow discharge-produced electrons into the second chamber well.

BRIEF DESCRIPTION OF THE DRAWINGS

FIGS. 3–5 are views of the discharge electrode assembly;

DETAILED DESCRIPTION OF AN ILLUSTRATIVE EMBODIMENT

Figure 1:
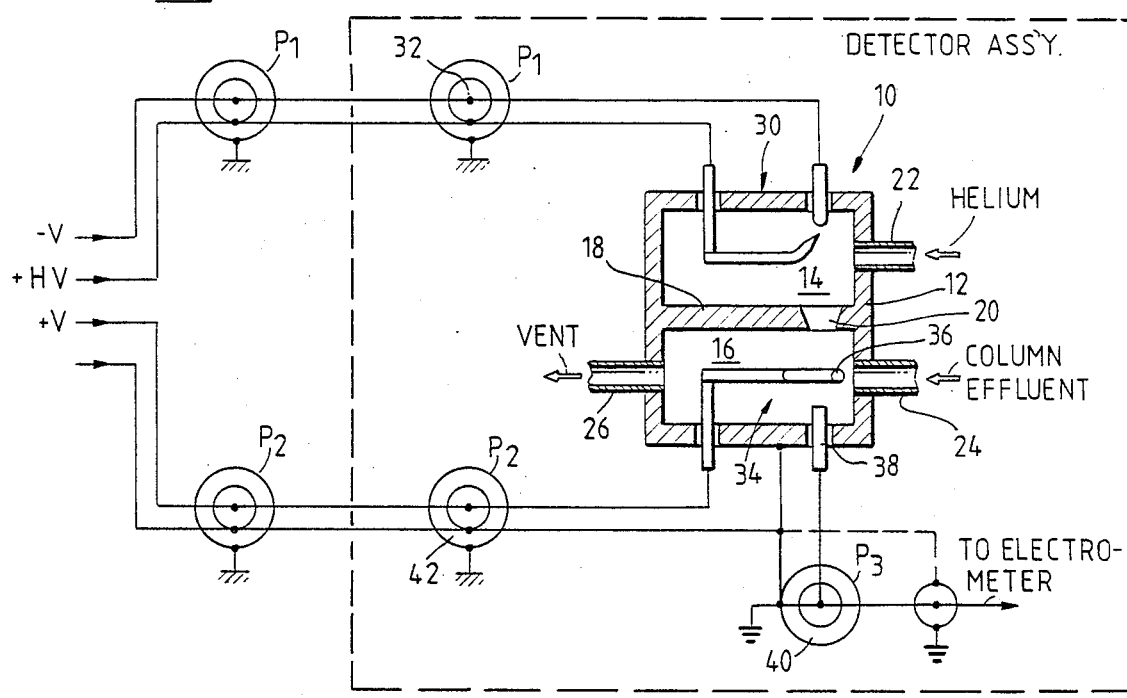
FIG. 1 is a diagram of a discharge ionization detector assembly in accordance with the present invention.

Referring to FIG. 1, there is shown a diagram of a discharge ionization detector assembly in accordance with the present invention. The detector assembly 10 generally includes a detector body 12 defining first and second chamber wells 14 and 16 which are coaxially disposed and have a common internal wall 18 with an aperture 20 therein. The body includes an inlet 22 for admitting an emission gas, preferably helium, and an inlet 24 to the second chamber well for admitting the column effluent of a chromatograph. A vent outlet 26 from the second chamber well 16 is also provided.

A first electrode assembly 30 is provided in the first chamber well 14. The electrode assembly includes a pair of electrodes for generating a glow discharge emission directed through the aperture 20 into the second chamber well 16 to cause ionization of species in the column effluent. The electrodes of the first electrode assembly 30 have a high voltage applied across them via an electrical connector 32.

A second electrode assembly 34 is provided in the second chamber well 16. The second electrode assembly includes a polarizing electrode 36, to be negatively charged, for generating an electric field with respect to the collector electrode 38 to cause electrons in the discharge emission to be repelled away from the collector electrode. The polarizing electrode 36 further causes electrons produced by the ionization of species in the column effluent to be accelerated toward the collector electrode. The collector electrode 38 is to be coupled to an electrometer by an electrical connector 40, so as to provide for an indication of ionized species in the column effluent. The polarizing electrode is provided with a negative charge by coupling through electrical connector 42 to a polarizing voltage source (not shown).

The column effluent input 24 to the second chamber well 16 directs the flow of column effluent transversely to the discharge emission entering the chamber through aperture 20. The polarizing electrode 36 is disposed within the second chamber so as to be substantially aligned with the column effluent inlet. Further, the polarizing electrode is of an annular configuration oriented in a plane transverse to the discharge emission. The collector electrode 34 is disposed in substantially coaxial alignment with the aperture 20.

Figure 2:
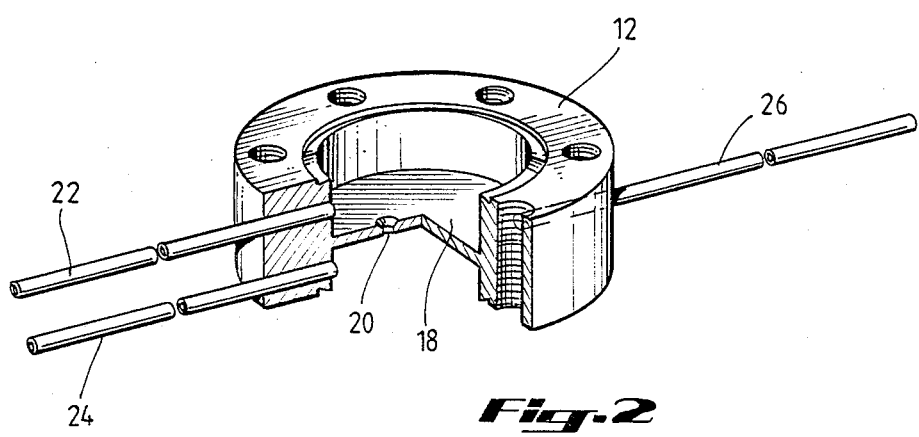
FIG. 2 is a section view of a detector body.

Referring now to FIG. 2, in an embodiment of the present invention, the detector body 12 is of a cylindrical configuration. The detector body may be of a one-piece, unitary construction having the first and second chamber wells machined therein. The emission gas inlet, column effluent inlet, and vent outlet may suitably be lengths of tubing extending through the sidewall of the detector body into the respective chamber well. The detector body itself is electrically conductive and is preferably made of a metal material or other electrically conductive materials. The geometry of aperture 20 is preferably such that the ratio of its length to its diameter is greater than one, and is on the order of five to ten. Such a geometry reduces back diffusion of eluted components into the large volume of the discharge chamber.

Subsequent elution from the discharge chamber causes "peak tailing" and less of resolution.

Referring to FIGS. 3-5, the discharge electrode assembly is illustrated. The electrode assembly is carried in a circular flange 44 adapted to be placed atop detector body 12 to enclose chamber well 14. The flange is held in position by a plurality of screws which pass through openings 45 arranged as indicated in FIGS. 3 and 5A, 5C. The discharge electrode assembly includes a pair of metallic elements 46 and 48 disposed within flange 44 by respective electrically-insulating sleeves 50 and 52 (FIG. 4). Elements 46 and 48 extend above and below the upper and lower planar surfaces of flange 44. As shown in FIGS. 5A and 5B, wire extensions 54 and 56 are attached to elements 46 and 48 above the upper surface of flange 44. An anode element 58 is attached to electrode element 48 on the underside of flange 44 (FIGS. 5B and 5C). The anode element is placed so as to provide a narrow arc gap between its tip end and electrode element 46. Connection of the discharge electrode assembly to a high voltage source is made via wires 54 and 56.

Figure 6:
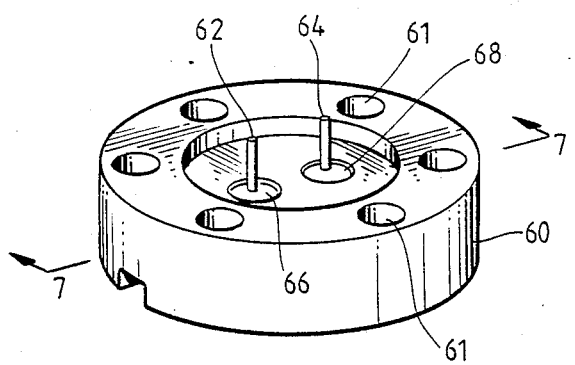
FIGS. 6–8 are views of the measurement electrode assembly.
Figure 7:
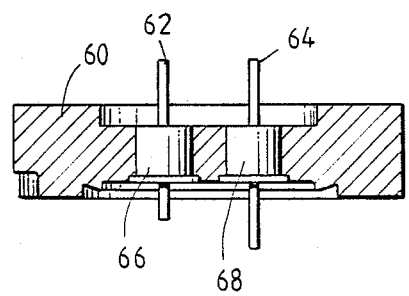
Figure 8A:
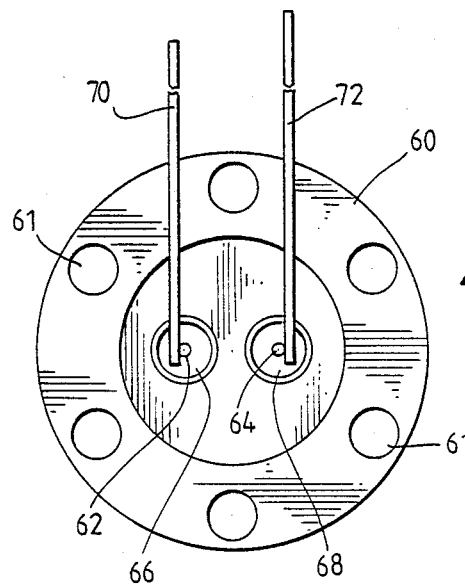
Figure 8C:
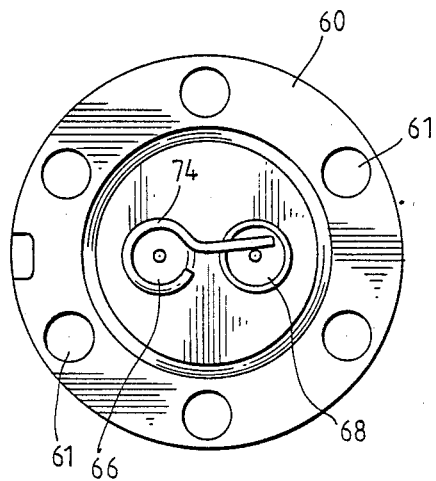
Figure 8B:
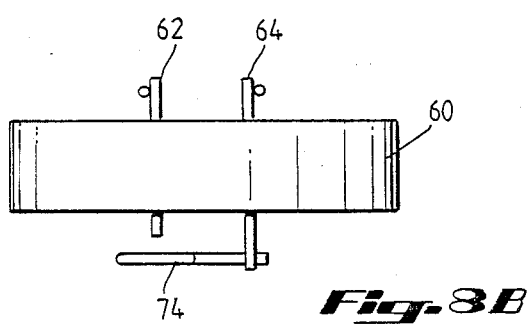

Referring next to FIGS. 6, 7 and 8, there is shown a flange 60 carrying the second electrode assembly. Flange 60 is adapted to be mounted to the detector body to enclose the second chamber well. Attachment of flange 60 is by threaded fasteners inserted through openings 61. The second electrode assembly includes electrode elements 62 and 64, which are mounted within flange 60 by electrically-insulating sleeves 66 and 68, respectively. The electrode elements 62 and 64 extend beyond the upper and lower surfaces of flange 60.

The electrode elements 62 and 64 are shown to have attached thereto wire extensions 70 and 72, respectively. Further, electrode element 64 has attached to it element 74 which defines an annular electrode structure. Element 74 is disposed concentrically with respect to the electrode element 62. In this measurement electrode assembly, element 74 provides a polarizing electrode having a negative potential thereon. The electrode element 62 is a collector electrode, which is coupled to ground potential.

Figure 9:
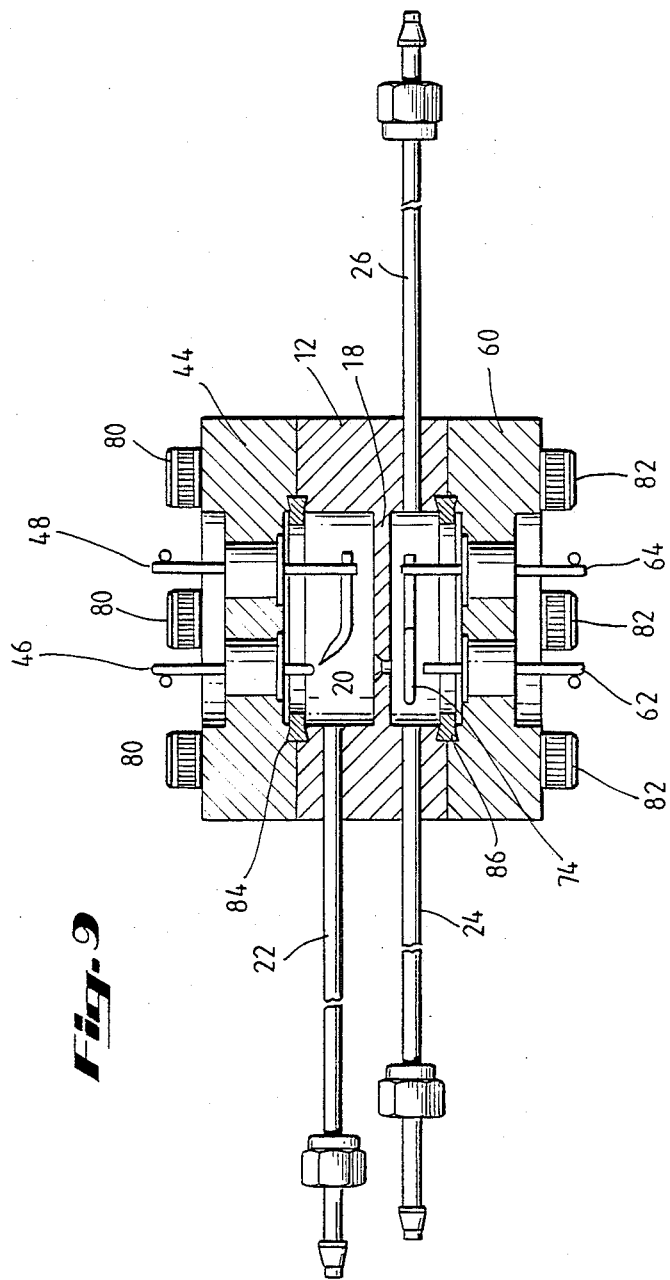
FIG. 9 shows the discharge and measurement electrode assemblies in place on the detector body.

Referring now to FIG. 9, an assembly of the detector elements is shown wherein the detector body 12 has the flange 44 mounted to the topside and the flange 60 mounted to the bottom side. Flanges 44 and 60 are mounted and held in place by screws 80 and 82, respectively. In FIG. 9, sectioning reveals the internal arrangement of the detector components. As shown, sealing of the flange and body interface against leakage is provided by a first gasket 84 and a second gasket 86. As further shown in FIG. 9, there is coaxial alignment of the electrode element 46 of the discharge electrode assembly, aperture 20 in wall 18 of body 12, annular electrode element 74 and collector electrode element 62 of the measurement electrode assembly.

The detector body 12 is conductive and coupled to ground potential. The internal wall 18 serves to block electrons generated in the discharge chamber 14 from reaching the ionization chamber 16. Those few electrons entering the ionization chamber through aperture 20 are substantially repelled by the polarizing electrode. The glow discharge emission of electrode assembly 30 is "exposed," which means that there is no shield or envelope surrounding the electrodes to provide containment of electrons produced by the glow discharge.

The foregoing description has been of but one implementation of the invention. Many modifications of the illustrated embodiment will be apparent to those skilled in the art. For example, the electrode 36 shown in FIG. 1 may be positively charged to cause collection of positive ions at electrode 38, resulting in positive current to the electrometer. Accordingly, it is the intention that the following claims cover all equivalent modifications and variations as fall within the scope of the invention.

What is claimed is:

1. A discharge ionization detector, comprising:
   a detector body of an electrically-conductive material defining first and second chamber wells coaxially disposed and having a common internal wall with an aperture therein;
   said body including an inlet to the first chamber well for admitting an emission gas, and an inlet to the second chamber well for admitting the column effluent of a chromatograph;
   said body having a single vent opening from the second chamber well in substantial coaxial alignment with the column effluent inlet;
   a first demountable electrode assembly including a flange and gasket seal to be mounted to the detector body to close the first chamber well, and having a pair of electrodes for generating an exposed glow discharge emission directed through the aperture into the second chamber well to cause ionization of species in the column effluent;
   a second demountable electrode assembly including a flange and gasket seal to be mounted to the detector body to close the second chamber well, and having a collector electrode, to be coupled to an electrometer providing an indication of ionized species in the column effluent, and a polarizing electrode, to be negatively charged, for generating an electric field with respect to the collector electrode to cause electrons produced by species ionization to be accelerated toward the collector electrode;
   the column effluent inlet to the second chamber well directing the flow of column effluent transversely to the discharge emission directed through the aperture;
   the polarizing electrode disposed within the second chamber to be substantially aligned with the column effluent inlet and being of an annular configuration oriented in a plane transverse to the discharge emission;
   the collector electrode disposed in substantially coaxial alignment with the aperture; and
   means for coupling said detector body to ground potential, to reduce the entry of glow discharge-produced electrons into the second chamber well.

2. The detector of claim 1 wherein the aperture in the detector body has a length to diameter ratio greater than one.

3. The detector of claim 1 wherein the aperture in the detector body has a length to diameter ratio within a range of about five to ten.

4. A discharge ionization detector, comprising:
   a detector body of an electrically-conductive material defining first and second chamber wells coaxially disposed and having a common internal wall with an aperture therein;
   said body including an inlet to the first chamber well for admitting an emission gas, and an inlet to the second chamber well for admitting the column effluent of a chromatograph;

said body having a single vent opening from the second chamber well;

a first demountable electrode assembly including a flange and gasket seal to be mounted to the detector body to close the first chamber well, and having a pair of electrodes for generating an exposed glow discharge emission directed through the aperture into the second chamber well to cause ionization of species in the column effluent;

a second demountable electrode assembly including a flange and gasket seal to be mounted to the detector body to close the second chamber well, and having a collector electrode, to be coupled to an electrometer providing an indication of ionized species in the column effluent, and a polarizing electrode, for generating an electric field with respect to the collector electrode to cause ionization species to be accelerated toward the collector electrode;

the column effluent inlet to the second chamber well directing the flow of column effluent transversely to the discharge emission directed through the aperture;

the polarizing electrode disposed within the second chamber to be substantially aligned with the column effluent inlet and being of an annular configuration oriented in a plane transverse to the discharge emission;

the collector electrode disposed in substantially coaxial alignment with the aperture; and means for coupling said detector body to ground potential, to reduce the entry of glow discharge-produced electrons into the second chamber well.

* * * * *